(12) United States Patent
Michihata et al.

(10) Patent No.: US 10,905,319 B2
(45) Date of Patent: Feb. 2, 2021

(54) ENDOSCOPE APPARATUS (71) Applicant: Sony Olympus Medical Solutions Inc., Tokyo (JP)

(72) Inventors: Taihei Michihata, Kanagawa (JP); Kohtaro Amano, Tokyo (JP); Morinao Fukuoka, Kanagawa (JP); Yuichi Yamada, Tokyo (JP)

(73) Assignee: Sony Olympus Medical Solutions Inc., Tokyo (JP)

(*) Notice: Subject to any disclaimer, the term of this patent is extended or adjusted under 35 U.S.C. 154(b) by 375 days.

(21) Appl. No.: 15/710,162

(22) Filed: Sep. 20, 2017

(65) Prior Publication Data
US 2018/0092520 A1 Apr. 5, 2018

(30) Foreign Application Priority Data
Oct. 3, 2016 (JP) .................. 2016-195913

(51) Int. Cl.
*A61B 1/05* (2006.01)
*A61B 1/00* (2006.01)
(Continued)

(52) U.S. Cl.
CPC ............ *A61B 1/05* (2013.01); *A61B 1/00013* (2013.01); *A61B 1/00114* (2013.01); *A61B 1/00117* (2013.01); *A61B 1/00124* (2013.01); *A61B 1/00135* (2013.01); *A61B 1/018* (2013.01); *A61B 1/042* (2013.01); *A61B 18/149* (2013.01); *G02B 23/2484* (2013.01); *A61B 2018/00178* (2013.01); *A61B 2018/00601* (2013.01);
(Continued)

(58) Field of Classification Search
CPC ... A61B 1/05; A61B 1/00114; A61B 1/00117; A61B 1/00124; A61B 1/00135; A61B 1/018; A61B 18/149
See application file for complete search history.

(56) References Cited

U.S. PATENT DOCUMENTS

2009/0247825 A1* 10/2009 Tanahashi .......... A61B 1/00039
600/110
2013/0012777 A1 1/2013 Baum
(Continued)

FOREIGN PATENT DOCUMENTS

JP 2003135385 A 5/2003
JP 2006181021 A 7/2006
(Continued)

*Primary Examiner* — Timothy J Neal
*Assistant Examiner* — William B Chou
(74) *Attorney, Agent, or Firm* — Xsensus LLP (57) ABSTRACT

An endoscope apparatus includes: a camera including an imaging unit configured to receive light and convert the light into an electric signal; a first cable configured to transmit the electric signal, one end of the first cable being connected to the camera; an operating unit connected to another end of the first cable and including an electrooptic conversion unit configured to convert the electric signal transmitted through the first cable into an optical signal, and a switch configured to receive user operations; a second cable configured to transmit the optical signal, one end of the second cable being connected to the operating unit; and a connector provided to another end of the second cable and configured to connect the other end of the second cable to an external device.

6 Claims, 4 Drawing Sheets (51) Int. Cl.
    *A61B 1/018*     (2006.01)
    *A61B 18/14*     (2006.01)
    *G02B 23/24*     (2006.01)
    *A61B 1/04*     (2006.01)
    *A61B 18/00*     (2006.01)

(52) U.S. Cl.
    CPC .............. *A61B 2018/00982* (2013.01); *A61B 2018/1475* (2013.01)

(56) References Cited

U.S. PATENT DOCUMENTS

| | | | |
|---|---|---|---|
| 2017/0049301 A1* | 2/2017 | Hagihara | A61B 1/042 |
| 2017/0184837 A1* | 6/2017 | Kang | H04N 5/232 |
| 2017/0303771 A1* | 10/2017 | Sudo | A61B 1/00013 |
| 2018/0368662 A1* | 12/2018 | Nakagawa | A61B 1/00117 |
| 2019/0000307 A1* | 1/2019 | Kawahara | A61B 1/00126 |

FOREIGN PATENT DOCUMENTS

| | | |
|---|---|---|
| JP | 2009233173 A | 10/2009 |
| JP | 2013000450 A | 1/2013 |
| JP | 2015-134039 | 7/2015 |
| JP | 2016010496 A | 1/2016 |
| WO | 2014171275 A | 10/2014 |

\* cited by examiner

ENDOSCOPE APPARATUS

CROSS-REFERENCE TO RELATED APPLICATION

The present application claims priority to and incorporates by reference the entire contents of Japanese Patent Application No. 2016-195913 filed in Japan on Oct. 3, 2016.

BACKGROUND

The present disclosure relates to an endoscope apparatus.

An endoscope apparatus that images the inside of a living body (a subject image) using an imaging element has been known in the field of medicine (refer to Japanese Laid-open Patent Publication No. 2015-134039, for example).

The endoscope apparatus described in Japanese Laid-open Patent Publication No. 2015-134039 includes a camera (a camera head) that is mounted on an endoscope (an insertion unit) inserted into the inside of a living body and has an imaging element that takes a subject image captured by the endoscope and a composite cable that transmits an imaging signal from the camera to a controller. The controller processes the imaging signal from the endoscope apparatus to generate a video signal for display and outputs the video signal to a display apparatus. With this processing, the display apparatus displays an observation image based on the video signal.

The endoscope apparatus described in Japanese Laid-open Patent Publication No. 2015-134039 uses optical transmission, which is large in the amount of information transmission, considering enhanced resolution of the imaging element and the like. In other words, the camera includes an electrooptic conversion unit that converts an imaging signal (an electric signal) by the imaging element into an optical signal. The composite cable includes optical fibers that transmit the imaging signal converted into the optical signal by the electrooptic conversion unit.

SUMMARY

In an endoscope apparatus for use in a resectoscope and the like, an operator treats living body tissue while the operator oneself holds the resectoscope inserted into the inside of a living body in a hand, and therefore downsizing and weight reduction are required for the camera mounted on the resectoscope.

However, in the endoscope apparatus described in Japanese Laid-open Patent Publication No. 2015-134039, the electrooptic conversion unit is provided in the camera, causing a problem in that the downsizing of the camera is hindered. In addition, the electrooptic conversion unit is provided in the camera, causing a problem in that the temperature of the camera may exceed a preset limit temperature owing to the heating of the electrooptic conversion unit corresponding to use.

An endoscope apparatus according to one aspect of the present disclosure may include: a camera including an imaging unit configured to receive light and convert the light into an electric signal; a first cable configured to transmit the electric signal, one end of the first cable being connected to the camera; an operating unit connected to another end of the first cable and including an electrooptic conversion unit configured to convert the electric signal transmitted through the first cable into an optical signal, and a switch configured to receive user operations; a second cable configured to transmit the optical signal, one end of the second cable being connected to the operating unit; and a connector provided to another end of the second cable and configured to connect the other end of the second cable to an external device.

DETAILED DESCRIPTION

The following describes embodiments for performing the present disclosure (hereinafter, embodiments) with reference to the accompanying drawings. The embodiments described below do not limit the present disclosure. Further, in the drawings, the same components are denoted by the same symbols.

First Embodiment

Schematic Configuration of Endoscope System

Figure 1:
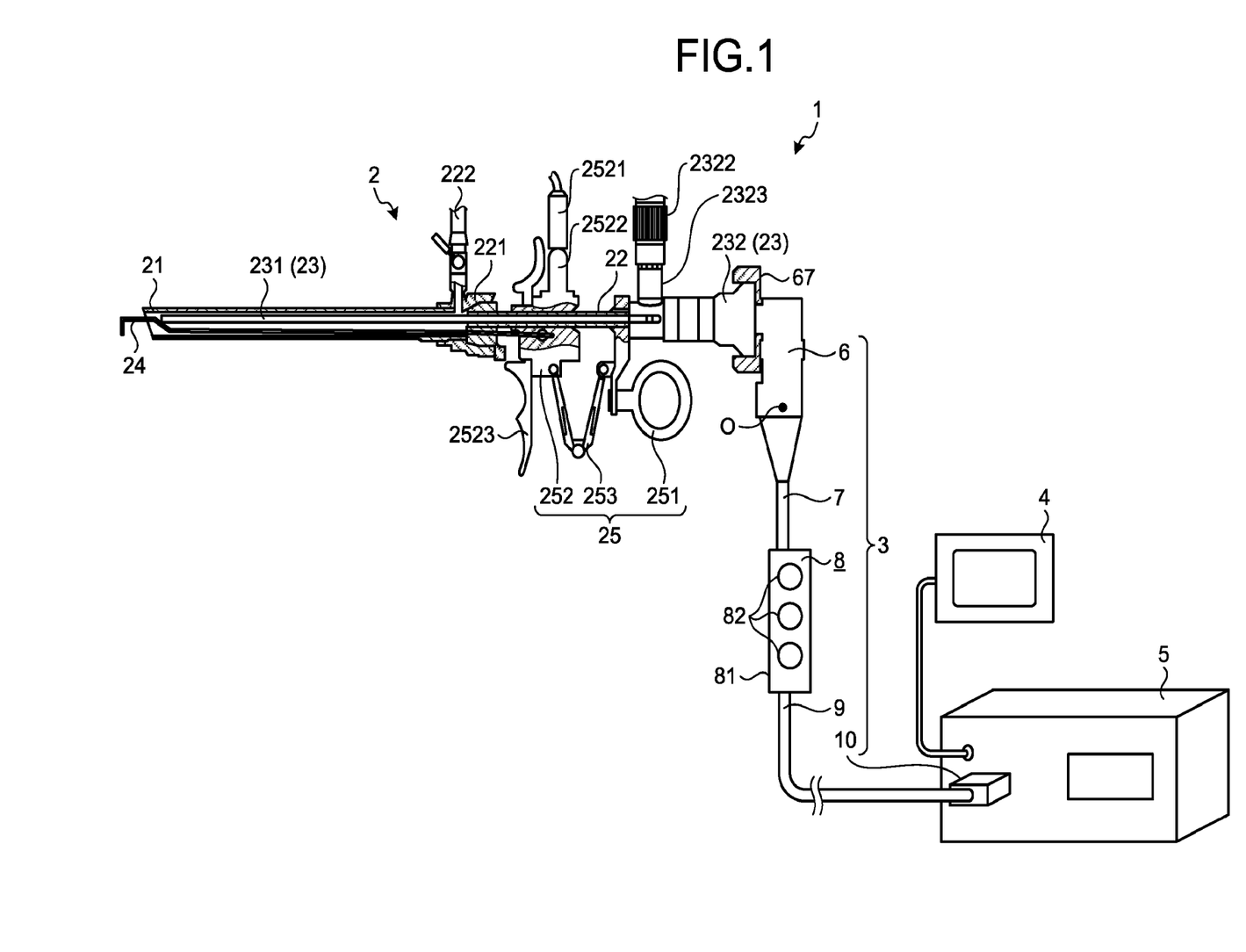
FIG. 1 is a diagram of a configuration of an endoscope system according to a first embodiment of the present disclosure.

FIG. 1 is a diagram of a configuration of an endoscope system 1 according to a first embodiment of the present disclosure.

The endoscope system 1 is a system that is used in the field of medicine and treats (incises or the like) living body tissue while observing the inside of a living body. As illustrated in FIG. 1, this endoscope system 1 includes a resectoscope 2, an imaging apparatus 3 for endoscope use, a display apparatus 4, and a controller 5.

The resectoscope 2 is a part that is inserted into the inside of a living body, captures a subject image, and treats living body tissue. As illustrated in FIG. 1, this resectoscope 2 includes a sheath 21, a guide pipe 22, an endoscope 23, a resectoscope electrode member 24, and a handle 25.

A "distal end" described below means an end on a side to be inserted into the inside of a living body (the left end in FIG. 1). A "basal end" described below means an end on a side separately from the "distal end" (the right end in FIG. 1).

The sheath 21 is a part having a cylindrical shape to be inserted into the inside of a living body.

The guide pipe 22 has an outer diametric dimension smaller than the inner diametric dimension of the sheath 21 and is inserted into the sheath 21 from the basal end side of the sheath 21. The distal end side of the guide pipe 22 is fixed to the basal end side of the sheath 21 via a mount member 221 (FIG. 1).

The mount member 221 is provided with a water supply inlet 222 for injecting liquid into the sheath 21 and supplying the liquid from the distal end of the sheath 21.

The endoscope 23 is a part that captures the subject image and includes an insertion unit 231 and an eyepiece unit 232 as illustrated in FIG. 1.

The insertion unit 231 is fixed to the inside of the guide pipe 22 and is inserted into the sheath 21. This insertion unit 231 incorporates an optical system that includes one or more lenses and collects the subject image.

The eyepiece unit 232 is coupled to the basal end of the insertion unit 231. This eyepiece unit 232 incorporates an eyepiece optical system 2321 (refer to FIG. 3) that emits the subject image collected by the optical system within the insertion unit 231 from the basal end of the eyepiece unit 232 to the outside. The eyepiece unit 232 is formed in a tapered shape having a more enlarged diameter toward the basal end; the imaging apparatus 3 for endoscope use is detachably connected to the enlarged diameter part.

Figure 3:
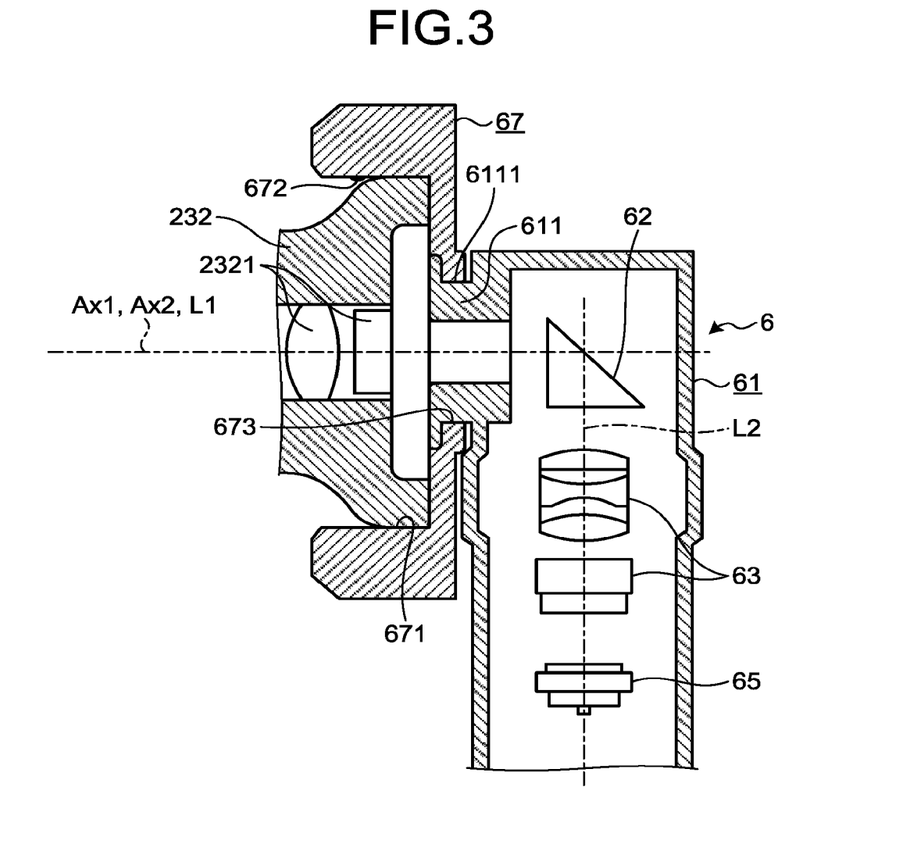
FIG. 3 is a sectional view of a connecting part between an eyepiece unit and a camera head.

The eyepiece unit 232 is provided with a light source connector 2323 to which a light guide 2322 is connected. In other words, light supplied from a light source apparatus (not illustrated) to the light guide 2322 is supplied to the insertion unit 231 via the eyepiece unit 232. The light supplied to the insertion unit 231 is emitted from the distal end of the insertion unit 231 to be applied to the inside of a living body. The light applied to the inside of a living body (the subject image) is emitted from the basal end of the eyepiece unit 232 via the optical system within the insertion unit 231 and the eyepiece optical system 2321.

The resectoscope electrode member 24 is inserted into the sheath 21 via the mount member 221, and the distal end thereof protrudes from the distal end of the sheath 21. The distal end part of the resectoscope electrode member 24 comes into contact with the living body tissue and treats the living body tissue through a high-frequency current.

The handle 25 is a part through which an operator holds the resectoscope 2 and operates the resectoscope electrode member 24. As illustrated in FIG. 1, this handle 25 includes a fixed ring 251, a slider 252, and a spring 253.

The fixed ring 251 is a part on which the operator hooks a thumb and that is fixed to the basal end side of the guide pipe 22.

The slider 252 is inserted into the guide pipe 22 and is movable in the right-and-left direction in FIG. 1 along the guide pipe 22.

As illustrated in FIG. 1, the basal end of the resectoscope electrode member 24 is fixed to this slider 252. In other words, the resectoscope electrode member 24 advances and retracts in the right-and-left direction in FIG. 1 within the sheath 21 along with the movement of the slider 252.

In addition, the slider 252 is provided with a power supply connector 2522 to which a high-frequency power supply cord 2521 connected to a high-frequency power supply (not illustrated) is connected. This power supply connector 2522 is electrically connected to the basal end of the resectoscope electrode member 24 via a lead wire (not illustrated).

Further, as illustrated in FIG. 1, the slider 252 is provided with a finger-hooking member 2523 on which the operator hooks fingers other than the thumb to move the slider 252 (advance and retract the resectoscope electrode member 24).

The spring 253 has a substantially U-shape; one end thereof is mounted on the fixed ring 251, whereas the other end thereof is mounted on the slider 252. The spring 253 biases the slider 252 to a side separating from the fixed ring 251.

In other words, the operator hooks the fingers on the fixed ring 251 and the finger-hooking member 2523 and pulls the finger-hooking member 2523 nearer against the biasing force of the spring 253, thereby moving the slider 252 to the basal end side (moving the resectoscope electrode member 24 to the basal end side). When the operator moves the fingers off the finger-hooking member 2523, the slider 252 (the resectoscope electrode member 24) moves toward the distal end side through the biasing force of the spring 253.

The imaging apparatus 3 for endoscope use has a function as an endoscope apparatus according to the present disclosure and is detachably connected to the eyepiece unit 232 of the resectoscope 2 (the endoscope 23). The imaging apparatus 3 for endoscope use takes the subject image captured by the endoscope 23 (the subject image emitted from the eyepiece unit 232) to generate an imaging signal (an image signal) under the control by the controller 5. The imaging apparatus 3 for endoscope use outputs multiple distributed image signals that are obtained by distributing the image signal and are different from each other.

A detailed configuration of the imaging apparatus 3 for endoscope use will be described below.

The display apparatus 4 includes a display using liquid crystals, electro luminescence, or the like. The display apparatus 4 displays an observation image based on a video signal processed by the controller 5 and the like.

The controller 5 corresponds to an external device according to the present disclosure. This controller 5 includes a central processing unit (CPU) and comprehensively controls the operation of the imaging apparatus 3 for endoscope use and the display apparatus 4.

Specifically, the controller 5 restores the multiple distributed image signals input from the imaging apparatus 3 for endoscope use to the original image signal and performs various kinds of image processing on the image signal to generate a video signal for display. The controller 5 outputs the video signal to the display apparatus 4. The controller 5 outputs a control signal, a sync signal, a clock, electric power, and the like to the imaging apparatus 3 for endoscope use.

Configuration of Imaging Apparatus for Endoscope Use

The following describes a configuration of the imaging apparatus 3 for endoscope use.

Figure 2:
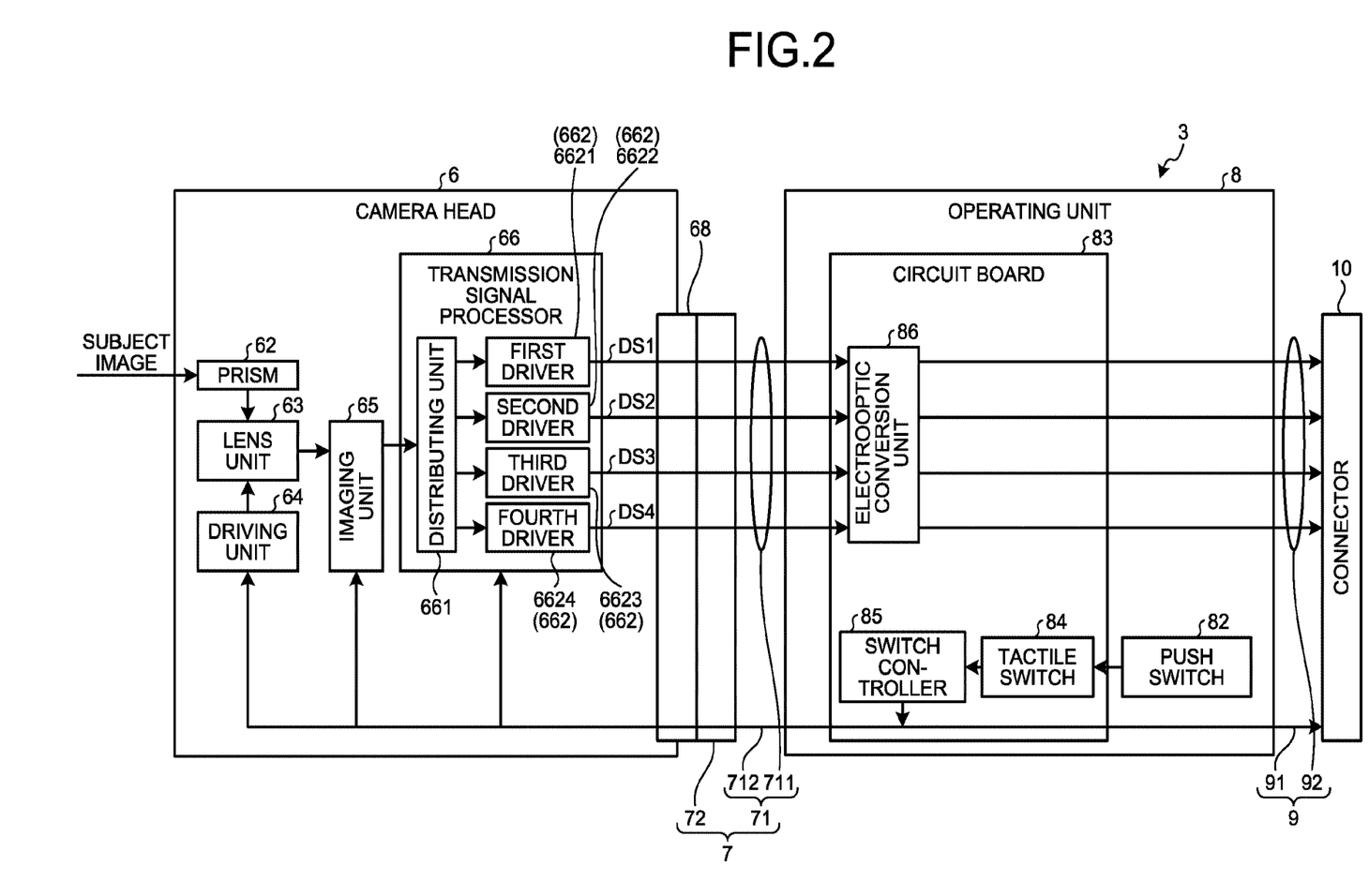
FIG. 2 is a block diagram of a configuration of an imaging apparatus for endoscope use.

FIG. 2 is a block diagram of the configuration of the imaging apparatus 3 for endoscope use.

As illustrated in FIG. 1 or FIG. 2, the imaging apparatus 3 for endoscope use includes a camera head 6, a first cable 7, an operating unit 8, a second cable 9, and a connector 10.

Configuration of Camera Head

FIG. 3 is a sectional view of a connecting part between the eyepiece unit 232 and the camera head 6. FIG. 3 omits the illustration of a driving unit 64 and a transmission signal processor 66 for the convenience of description.

As illustrated in FIG. 1 or FIG. 3, the camera head 6 is a part that is detachably connected to the eyepiece unit 232 of the endoscope 23 and has a function as a camera according to the present disclosure. As illustrated in FIG. 2 or FIG. 3, this camera head 6 includes a camera head casing 61 (FIG. 3), a prism 62, a lens unit 63, the driving unit 64 (FIG. 2), an imaging unit 65, and the transmission signal processor 66 (FIG. 2) housed in the camera head casing 61.

The camera head casing 61 is a casing housing the members 62 to 66.

As illustrated in FIG. 3, this camera head casing 61 is provided with a protrusion 611 having a cylindrical shape that causes the inside and the outside of the camera head casing 61 to communicate with each other. Formed on the outer peripheral surface of this protrusion 611 is an annular grove 6111 extending in a rotational direction about a central axis Ax1 of the protrusion 611. A mount member 67 is mounted on the annular grove 6111.

The mount member 67 is a member for mounting the camera head 6 on the eyepiece unit 232 and has a cylindrical shape.

This mount member 67 is provided with a fitting hole 671 that is recessed toward the other end and into which the eyepiece unit 232 fit on an end face on one end thereof. Provided on the inner peripheral face of the fitting hole 671 is a locking protrusion 672 locking on the outer peripheral face of the eyepiece unit 232. With the eyepiece unit 232 fitting into the fitting hole 671, an optical axis L1 of the endoscope 23 overlaps with a central axis Ax2 of the mount member 67.

The mount member 67 is provided with a communicating hole 673 communicating with the fitting hole 671 on an end face on the other end thereof. An edge of the communicating hole 673 fits into the annular grove 6111, whereby the mount member 67 is mounted on the protrusion 611. In this state, the central axis Ax2 of the mount member 67 and the central axis Ax1 of the protrusion 611 overlap with each other. The mount member 67 is rotatable about the central axis Ax1 (Ax2).

Consequently, the camera head 6 is rotatable about the optical axis L1 relative to the eyepiece unit 232 of the endoscope 23 via the mount member 67. The camera head 6 has its center of gravity O (FIG. 1) at a position (a position below the optical axis L1 in FIG. 3) apart from the optical axis L1 (a rotational central axis relative to the eyepiece unit 232). The camera head 6 rotates about the optical axis L1 irrespective of the rotation of the resectoscope 2 about the optical axis L1 to constantly have an attitude causing an optical axis L2 (FIG. 3) set within the camera head casing 61 to be along the vertical direction (an attitude in which the center of gravity O is positioned below the optical axis L1).

As illustrated in FIG. 3, the prism 62 is arranged on the central axis Ax1 of the protrusion 611 (on the optical axis L1) and deflects the travel direction of the subject image captured by the endoscope 23. Specifically, the prism 62 deflects the travel direction of the subject image emitted from the eyepiece unit 232 and captured within the camera head casing 61 via the protrusion 611 (the subject image traveling along the optical axis L1) by substantially 90 degrees and causes the subject image to travel along the optical axis L2.

As illustrated in FIG. 3, the lens unit 63 is arranged on the optical axis L2. The lens unit 63 includes one or multiple lenses and focuses the subject image via the prism 62 onto an imaging plane of the imaging unit 65. The lens unit 63 includes an optical zooming mechanism (not illustrated) that moves the one or multiple lenses to change the angle of view and a focusing mechanism (not illustrated) that changes the focus.

The driving unit 64 operates the optical zooming mechanism and the focusing mechanism to change the angle of view and the focus of the lens unit 63 under the control by the controller 5 or the operating unit 8.

As illustrated in FIG. 3, the imaging unit 65 is arranged on the optical axis L2. The imaging unit 65 takes the subject image focused by the lens unit 63 under the control by the controller 5. This imaging unit 65 includes a sensor chip that integrally forms an imaging element (not illustrated) such as a charge coupled device (CCD) or a complementary metal oxide semiconductor (CMOS) that receives the subject image focused by the lens unit 63 and converts the subject image into an electric signal, a signal processor (not illustrated) that performs signal processing (A/D conversion and the like) on the electric signal (an analog signal) from the imaging element to output an image signal, and the like and outputs the image signal after the A/D conversion (a digital signal). The signal processor (not illustrated) may be separately from the imaging element (not illustrated) without being integrally formed therewith.

The transmission signal processor 66 performs various kinds of processing on the image signal from the imaging unit 65. This transmission signal processor 66 includes a distributing unit 661 and multiple drivers 662.

The distributing unit 661 distributes (executes mapping processing on) the image signal from the imaging unit 65 to generate multiple (four in the present first embodiment) first to fourth distributed image signals DS1 to DS4 that are different from each other.

The multiple drivers 662 are provided in accordance with the number of the distributed image signals generated by the distributing unit 661. In other words, in the present first embodiment, as illustrated in FIG. 2, the drivers 662 include four first to fourth drivers 6621 to 6624. The four first to fourth drivers 6621 to 6624 perform encoding processing (N-bit/M (>N)-bit conversion processing (8-bit/10-bit conversion processing, for example)) and the like on the first to fourth distributed image signals DS1 to DS4, respectively, generated by the distributing unit 661.

The transmission signal processor 66 described above includes a programmable logic device such as a field-programmable gate array (FPGA), for example.

The first to fourth distributed image signals DS1 to DS4 processed by the transmission signal processor 66 are output to the first cable 7 via a first connector 68.

The first connector 68 is electrically connected to the transmission signal processor 66 (the first to fourth drivers 6621 to 6624) and is mounted on the camera head casing 61 so as to cause part thereof to be exposed out of the camera head casing 61. Examples of the first connector 68 include a hermetic connector.

Configuration of First Cable

As illustrated in FIG. 2, the first cable 7 includes a cable main body 71 and a second connector 72 that is provided to one end of the cable main body 71 and is detachably connected to the first connector 68.

The cable main body 71 is detachably connected to the camera head 6 (the first connector 68) via the second connector 72, whereas the other end thereof is connected to the operating unit 8. Specifically, the cable main body 71 arranges multiple electric wires 711 and 712 inside an outer sheath as an outermost layer.

The multiple (four in the present first embodiment) electric wires 711 are electric wires for transmitting the first to fourth distributed image signals DS1 to DS4 output from the camera head 6 (the first to fourth drivers 6621 to 6624) to the operating unit 8.

The multiple electric wires 712 are electric wires for transmitting a control signal, a sync signal, a clock, electric power, and the like output from the controller 5 and via the members 8 to 10 and a control signal and the like output from the operating unit 8 to the camera head 6. FIG. 2 illustrates only one of the multiple electric wires 712 for the convenience of description.

As described above, the camera head 6 and the operating unit 8 are detachably connected to each other via the first and second connectors 68 and 72. In other words, the first and second connectors 68 and 72 have a function as a connector according to the present disclosure.

Configuration of Operating Unit

Figure 4:
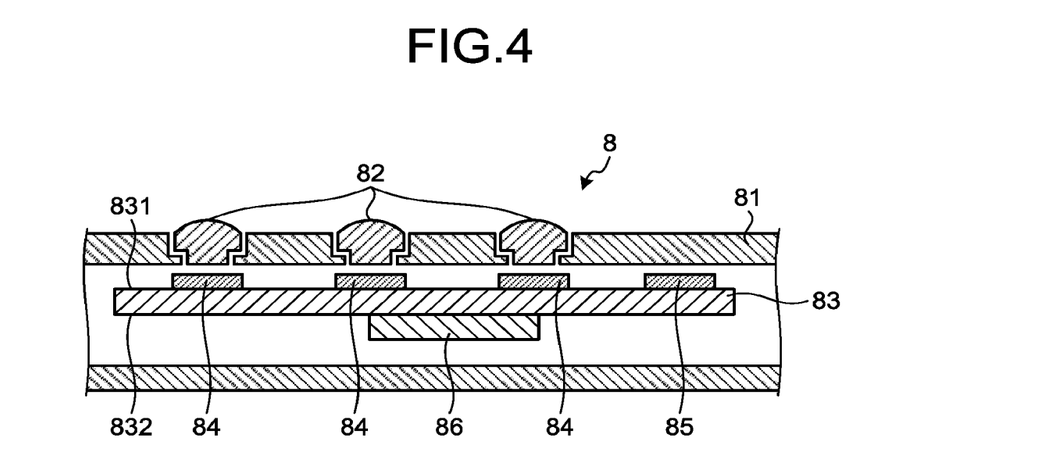
FIG. 4 is a sectional view of a configuration of an operating unit.

FIG. 4 is a sectional view of a configuration of the operating unit 8. FIG. 4 omits the illustration of connecting parts with the first and second cables 7 and 9 for the convenience of description.

The operating unit 8 relays the control signal, the sync signal, the clock, the electric power, the multiple distributed image signals, and the like transmitted between the camera head 6 and the controller 5 and receives various kinds of operations from the operator. As illustrated in FIG. 2 or FIG. 4, this operating unit 8 includes an operating casing 81 (FIG. 4), multiple push switches 82, a circuit board 83, multiple tactile switches 84, a switch controller 85, and an electrooptic conversion unit 86.

The operating casing 81 is a casing housing the members 83 to 86.

The multiple push switches 82 are mounted on the operating casing 81 with part thereof exposed out of the operating casing 81 and receive various kinds of operations from the operator.

Examples of the various kinds of operations from the operator include an instruction to adjust the image quality (white balance adjustment, brightness adjustment, and the like) of the observation image and an instruction to change the angle of view and the focus of the lens unit 63.

Although FIG. 1 and FIG. 4 illustrate three push switches 82, the number thereof is not limited to three and may be other numbers (including one).

The circuit board 83 is a rigid board on which the multiple tactile switches 84, the switch controller 85, and the electrooptic conversion unit 86 are mounted and that is electrically connected to the first cable 7 (the multiple electric wires 711 and 712) and the second cable 9 (multiple electric wires 91). The circuit board 83 relays the first to fourth distributed image signals DS1 to DS4 output from the camera head 6 and via the first cable 7 (the multiple electric wires 711) to the electrooptic conversion unit 86. The circuit board 83 relays the control signal, the sync signal, the clock, the electric power, and the like output from the controller 5 and via the second cable 9 (the multiple electric wires 91) to the first cable 7 (the multiple electric wires 712) and relays a control signal output from the switch controller 85 to the first cable 7 (the multiple electric wires 712) or the second cable 9 (the multiple electric wires 91).

The multiple tactile switches 84 have a function as at least one switch according to the present disclosure. These multiple tactile switches 84 are mounted on one face 831 (FIG. 4) of the circuit board 83 and face the respective multiple push switches 82 with the circuit board 83 arranged within the operating casing 81. The tactile switches 84 output instruction signals in accordance with operation on the push switches 82 (pressing) by the operator.

The switch controller 85 is mounted on the one face 831 of the circuit board 83 and outputs the control signal to the camera head 6 via the first cable 7 (the multiple electric wires 712) or to the controller 5 via the second cable 9 (the multiple electric wires 91) in accordance with the instruction signals from the multiple tactile switches 84.

When any of the multiple push switches 82 has received an instruction to adjust the image quality (white balance adjustment, brightness adjustment, and the like) of the observation image, for example, the switch controller 85 outputs the control signal responsive to the instruction to the controller 5 via the second cable 9 (the multiple electric wires 91). When any of the multiple push switches 82 has received an instruction to change the angle of view or the focus of the lens unit 63, the switch controller 85 outputs the control signal responsive to the instruction to the camera head 6 (the driving unit 64) via the first cable (the multiple electric wires 712).

The electrooptic conversion unit 86 is mounted on another face 832 opposite to the one face 831 of the circuit board 83. In other words, the multiple tactile switches 84 and the switch controller 85 and the electrooptic conversion unit 86 are mounted on the different faces 831 and 832, respectively, of the circuit board 83. The electrooptic conversion unit 86 converts the first to fourth distributed image signals DS1 to DS4 (electric signals) output from the camera head 6, via the first cable 7 (the multiple electric wires 711), and relayed by the circuit board 83 into respective optical signals.

Configurations of Second Cable and Connector

The connector 10 includes a composite connector for transmitting both an electric signal and an optical signal and is provided to one end of the second cable 9.

The second cable 9 is detachably connected to the controller 5 via the connector 10 provided to the one end thereof, whereas the other end is connected to the operating unit 8 (the circuit board 83). Specifically, the second cable 9 is a composite cable that arranges the multiple electric wires 91 (FIG. 2) and multiple optical fibers 92 (FIG. 2) inside an outer sheath as an outermost layer.

The multiple electric wires 91 are electric wires for transmitting the control signal, the sync signal, the clock, the electric power, and the like output from the controller 5 and via the connector 10 to the operating unit 8 and transmitting the control signal and the like output from the operating unit 8 to the controller 5. FIG. 2 illustrates only one of the multiple electric wires 91 for the convenience of description.

The multiple (four in the present first embodiment) optical fibers 92 are optical fibers respective one ends of which are connected to the electrooptic conversion unit 86 and for transmitting the first to fourth distributed image signals DS1 to DS4 (optical signals) output from the electrooptic conversion unit 86 to the controller 5.

The number of the distributed image signals distributed by the distributing unit 661 is not limited to four, and the number of distribution may be other numbers. When the number of the distributed image signals has been changed, the respective numbers of the drivers 662, the electric wires 711, and the optical fibers 92 may be the number of the distributed image signals.

In the imaging apparatus 3 for endoscope use according to the present first embodiment described above, the electrooptic conversion unit 86 is provided in the operating unit 8 connected to the camera head 6 via the first cable 7. With this configuration, the electrooptic conversion unit 86 does not hinder the downsizing of the camera head 6. The electrooptic conversion unit 86 is provided in the operating unit 8 positioned separately from the camera head 6, and the camera head 6 may therefore be avoided from being influenced by the heating of the electrooptic conversion unit 86.

Consequently, the imaging apparatus 3 for endoscope use according to the present first embodiment produces an advantageous effect of making it possible to downsize the camera head 6 and to avoid an increase in the temperature of the camera head 6.

In particular, the imaging apparatus 3 for endoscope use is used for the resectoscope 2 that the operator oneself holds in a hand, and the camera head 6 is downsized, whereby the handleability of the resectoscope 2 by the operator may be improved.

In the imaging apparatus 3 for endoscope use according to the present first embodiment, the camera head 6 is mounted on the eyepiece unit 232 rotatably about the optical axis L1 of the endoscope 23 and has the center of gravity O at the position apart from the optical axis L1. With this configuration, even when the resectoscope 2 is rotated about the optical axis L1, the optical axis L2 of the camera head 6 may be maintained at the attitude along the vertical direction. Consequently, the display apparatus 4 may constantly display an erect observation image.

The operating unit 8 is connected to the camera head 6 via the first cable 7. With this configuration, even when the operating unit 8 moves through an operating force acting on the operating unit 8 by the operator during the operation, the movement is absorbed by the first cable 7 and may be avoided from transmitting to the camera head 6. In other words, the blurring of the observation image caused by the operation on the operating unit 8 may be avoided.

In the imaging apparatus 3 for endoscope use according to the present first embodiment, the operating unit 8 includes the circuit board 83 on which the multiple tactile switches 84 and the switch controller 85 are mounted on the one face 831 and on which the electrooptic conversion unit 86 is mounted on the other face 832. With this configuration, the operating unit 8 has a smaller board area than a configuration in which the multiple tactile switches 84, the switch controller 85, and the electrooptic conversion unit 86 are mounted on the one face 831 of the circuit board 83, for example, and the downsizing of the operating unit 8 may be achieved.

In the imaging apparatus 3 for endoscope use according to the present first embodiment, the camera head 6 and the operating unit 8 are detachably connected to each other via the first and second connectors 68 and 72. With this configuration, the imaging apparatus 3 for endoscope use may reduce an exchange unit when either the camera head 6 or the operating unit 8 has broken down compared with a configuration in which the camera head 6 and the operating unit 8 are integrally formed (undetachably) via the first cable 7 and may improve convenience.

Second Embodiment

The following describes a second embodiment of the present disclosure.

In the following section, components similar to those of the first embodiment will be denoted by the same symbols, and detailed descriptions thereof will be omitted or simplified.

Figure 5:
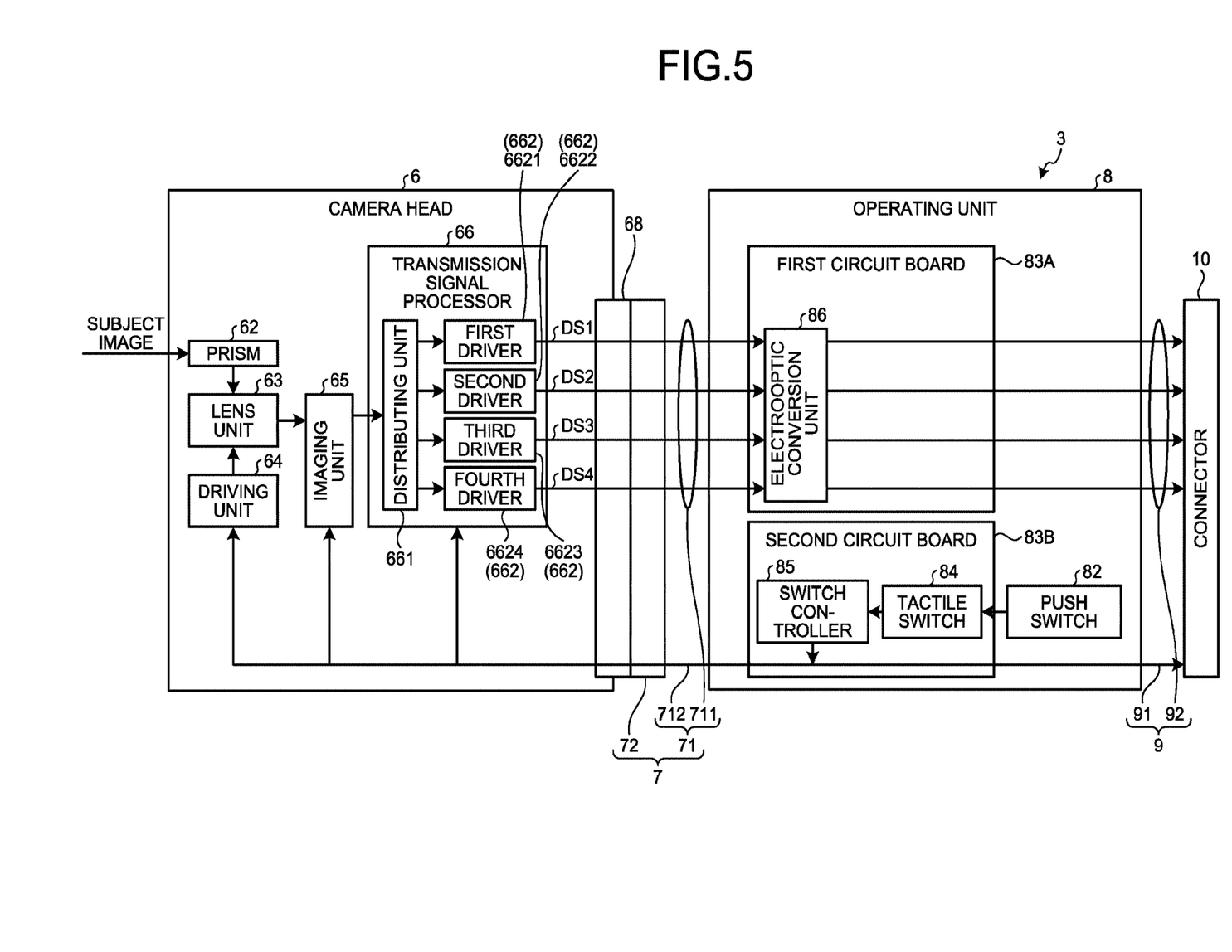
FIG. 5 is a block diagram of a configuration of an imaging apparatus for endoscope use according to a second embodiment of the present disclosure.

FIG. 5 is a block diagram of an imaging apparatus 3A for endoscope use according to the second embodiment of the present disclosure.

In the imaging apparatus 3 for endoscope use (the operating unit 8) according to the first embodiment, the multiple tactile switches 84, the switch controller 85, and the electrooptic conversion unit 86 are mounted on the one circuit board 83.

In contrast, in the imaging apparatus 3A for endoscope use (an operating unit 8A) according to the present second embodiment, as illustrated in FIG. 5, the multiple tactile switches 84 and the switch controller 85 and the electrooptic conversion unit 86 are mounted on first and second circuit boards 83A and 83B, respectively, that are independent of each other.

The first circuit board 83A includes a rigid board on which the electrooptic conversion unit 86 is mounted and that is electrically connected to the first cable 7 (the multiple electric wires 711). The first circuit board 83A relays the first to fourth distributed image signals DS1 to DS4 output from the camera head 6 and via the first cable 7 (the multiple electric wires 711) to the electrooptic conversion unit 86.

The second circuit board 83B includes a rigid board on which the multiple tactile switches 84 and the switch controller 85 are mounted and that is electrically connected to the first cable 7 (the multiple electric wires 712) and the second cable 9 (the multiple electric wires 91). The second circuit board 83B relays the control signal, the sync signal, the clock, the electric power, and the like output from the controller 5 and via the second cable 9 (the multiple electric wires 91) to the first cable (the multiple electric wires 712) and relays the control signal output from the switch controller 85 to the first cable 7 (the multiple electric wires 712) or the second cable 9 (the multiple electric wires 91).

The first and second circuit boards 83A and 83B described above are arranged within the operating casing 81 with their board faces facing each other.

The imaging apparatus 3A for endoscope use according to the present second embodiment described above produces the following effect apart from an effect similar to that of the first embodiment.

When one ends of the optical fibers 92 are connected to the electrooptic conversion unit 86 with the multiple tactile switches 84, the switch controller 85, and the electrooptic conversion unit 86 mounted on a circuit board, the workability of the connection may degrade owing to the multiple tactile switches 84 and the switch controller 85.

In the imaging apparatus 3A for endoscope use according to the present second embodiment, the operating unit 8A includes the first circuit board 83A on which the electrooptic conversion unit 86 is mounted and the second circuit board 83B that is formed separately from the first circuit board 83A and on which the multiple tactile switches 84 and the switch controller 85 are mounted. With this configuration, the operating unit 8A may be easily manufactured without the degradation of the workability of the connection.

Other Embodiments

The embodiments for performing the present disclosure have been described; the present disclosure should not be limited by the first and second embodiments alone.

Although the first and second embodiments exemplify the case in which the imaging apparatus 3 for endoscope use according to the present disclosure is used for the resectoscope 2, this is not limiting; the imaging apparatus 3 for endoscope use may be used for various other kinds of endoscopes (a hard endoscope or a soft endoscope). The camera according to the present disclosure is not limited to the camera head 6 that is detachably connected to the endoscope; an insertion unit of a distal end sensor type in which an image sensor (an imaging unit) is arranged at the distal end of the insertion unit may be configured as the camera according to the present disclosure, for example.

Although the multiple tactile switches 84, the switch controller 85, and the electrooptic conversion unit 86 in the first and second embodiments may be mounted on the circuit board 83 (the first and second circuit boards 83A and 83B), this is not limiting; other electronic components may be mounted.

In the camera head 6, at least part of the transmission signal processor 66 is omitted, for example, and the at least part of the transmission signal processor 66 may be mounted on the circuit board 83 (the first and second circuit boards 83A and 83B).

On the circuit board 83 (the first and second circuit boards 83A and 83B), a memory may be mounted that stores therein specific information of the imaging unit 65 (the imaging element), configuration data for constructing multiple functional blocks (the distributing unit 661 and the first to fourth drivers 6621 to 6624) in the transmission signal processor 66 (FPGA), and the like, for example. Examples of the specific information include information for use in the image processing by the controller 5, the information indicating the address of pixel defects of the imaging element.

In the first and second embodiments, the thickness of the operating casing 81 on a side in which the electrooptic conversion unit 86 is arranged may be larger than the other part. With this configuration, the heat of the electrooptic conversion unit 86 may be avoided from transmitting to the hand or fingers of the operator who operates the operating unit 8 (8A).

In the first and second embodiments, in place of the push switches 82, switching type, joystick type, or dial type switches may be employed. In place of the tactile switches 84, magnetic sensor type or photosensor type switches may be employed.

In the endoscope apparatus according to the present disclosure, the electrooptic conversion unit is provided in the operating unit connected to the camera via the first cable. With this configuration, the electrooptic conversion unit does not hinder the downsizing of the camera. In addition, the electrooptic conversion unit is provided in the operating unit positioned separately from the camera, and the camera may be avoided from being influenced by the heating of the electrooptic conversion unit.

Consequently, the endoscope apparatus according to the present disclosure produces an advantageous effect of making it possible to downsize the camera and to avoid an increase in the temperature of the camera.

It should be understood by those skilled in the art that various modifications, combinations, sub-combinations and alterations may occur depending on design requirements and other factors insofar as they are within the scope of the appended claims or the equivalents thereof.

What is claimed is:

1. An endoscope apparatus comprising:
   a camera including an imaging circuit configured to receive light and convert the light into an electric signal;
   a first cable configured to transmit the electric signal, one end of the first cable being connected to the camera;
   operating circuitry connected to another end of the first cable and including
      an electrooptic conversion circuit configured to convert the electric signal transmitted through the first cable into an optical signal, and
      a switch circuit configured to receive user operations, the electrooptic conversion circuit and the switch circuit being included in an operating casing, the operating casing being provided outside the camera;
   a second cable, having an optical fiber, configured to transmit the optical signal, the optical signal being carried in the optical fiber, one end of the second cable being connected to the operating circuitry; and
   a connector provided to another end of the second cable and configured to connect the other end of the second cable to an external device, wherein
   the camera is to be inserted into a subject, and is detachably connected to an eyepiece unit of an endoscope that is configured to capture a subject image of the subject, and
   the imaging circuit is configured to receive the subject image captured by the endoscope and convert the subject image into the electric signal.

2. The endoscope apparatus according to claim 1, wherein the endoscope is a hard endoscope.

3. The endoscope apparatus according to claim 1, wherein the camera is mounted on the eyepiece unit rotatably about an optical axis of the endoscope and has a center of gravity at a position apart from the optical axis.

4. The endoscope apparatus according to claim 1, wherein the operating circuitry comprises a circuit hoard having one face on which the switch circuit is mounted and another face opposite to the one face on which the electrooptic conversion circuit is mounted.

5. The endoscope apparatus according to claim 1, wherein the operating circuitry comprises:
   a first circuit board on which the electrooptic conversion circuit is mounted; and
   a second circuit board that is formed separately from the first circuit board and on which the switch circuit is mounted.

6. The endoscope apparatus according to claim 1, wherein the camera and the operating circuitry are detachably connected to each other via a connector.

* * * * *